(12) United States Patent
Tokur

(10) Patent No.: US 10,478,193 B2
(45) Date of Patent: Nov. 19, 2019

(54) CATHETER MAINTAINING BLOOD FLOW BY VEIN BYPASS

(71) Applicant: BEBILLER YAZILIM MEDIKAL ENDUSTRIYEL TARIMSAL ARASTIRMALAR VE TARIM URUNLERI TICARET VE SANAYI LIMITED SIRKETI, Kahramanmaras (TR)

(72) Inventor: Mahmut Tokur, Kahramanmaraş (TR)

(73) Assignee: BEBILLER YAZILIM MEDIKAL ENDUSTRIYEL TARIMSAL ARASTIRMALAR VE TARIM URUNLERI TICARET VE SANAYI LIMITED SIRKETI, Kahramanmaras (TR)

( * ) Notice: Subject to any disclaimer, the term of this patent is extended or adjusted under 35 U.S.C. 154(b) by 346 days.

(21) Appl. No.: 15/531,726

(22) PCT Filed: Nov. 28, 2014

(86) PCT No.: PCT/TR2014/000478
§ 371 (c)(1),
(2) Date: May 30, 2017

(87) PCT Pub. No.: WO2016/085420
PCT Pub. Date: Jun. 2, 2016

(65) Prior Publication Data
US 2017/0311955 A1    Nov. 2, 2017

(51) Int. Cl.
*A61B 17/12* (2006.01)
*A61M 25/10* (2013.01)
*A61B 17/11* (2006.01)

(52) U.S. Cl.
CPC .. *A61B 17/12045* (2013.01); *A61B 17/12109* (2013.01); *A61B 17/12136* (2013.01);
(Continued)

(58) Field of Classification Search
CPC ........ A61B 17/12045; A61B 17/12109; A61B 17/12136; A61B 2017/1107;
(Continued)

(56) References Cited

U.S. PATENT DOCUMENTS

| 4,840,690 A | 6/1989 | Melinyshyn et al. |
| 7,470,248 B1 | 12/2008 | Connelly et al. |

(Continued)

FOREIGN PATENT DOCUMENTS

WO    WO 2013/119879 A1    8/2013

OTHER PUBLICATIONS

International Search Report, dated Jul. 24, 2015 for corresponding International Application No. PCT/TR2014/000478.
(Continued)

*Primary Examiner* — Leslie R Deak
(74) *Attorney, Agent, or Firm* — Crose Law LLC; Bradley D. Crose

(57) ABSTRACT

A catheter (1) and vein repair method that enables vein repair surgeries without any bleeding and without hindering blood flow in veins through bypassing the blood flow in the vein to be operated and by preventing any diseases arisen due to stop of blood flow of the organ fed by the associated vein and that sustains blood flow by means of vein bypass in the course of vascular surgeries implemented for surgical processes related to veins in human body and that comprises one balloon (3) on each point close to its both ends, protective layer (4) positioned on the balloons (3); second path (5) enabling deflation inflation of the balloons (3), having monolithic pipe shape adhered to the first path (2) side by side, whose one open end terminates within the balloon (3); check valve apparatus (7) that is monolithic with back end of the second path (5) and provides substances such as air and liquid with the injector for inflation deflation (Continued)

Figure 1:
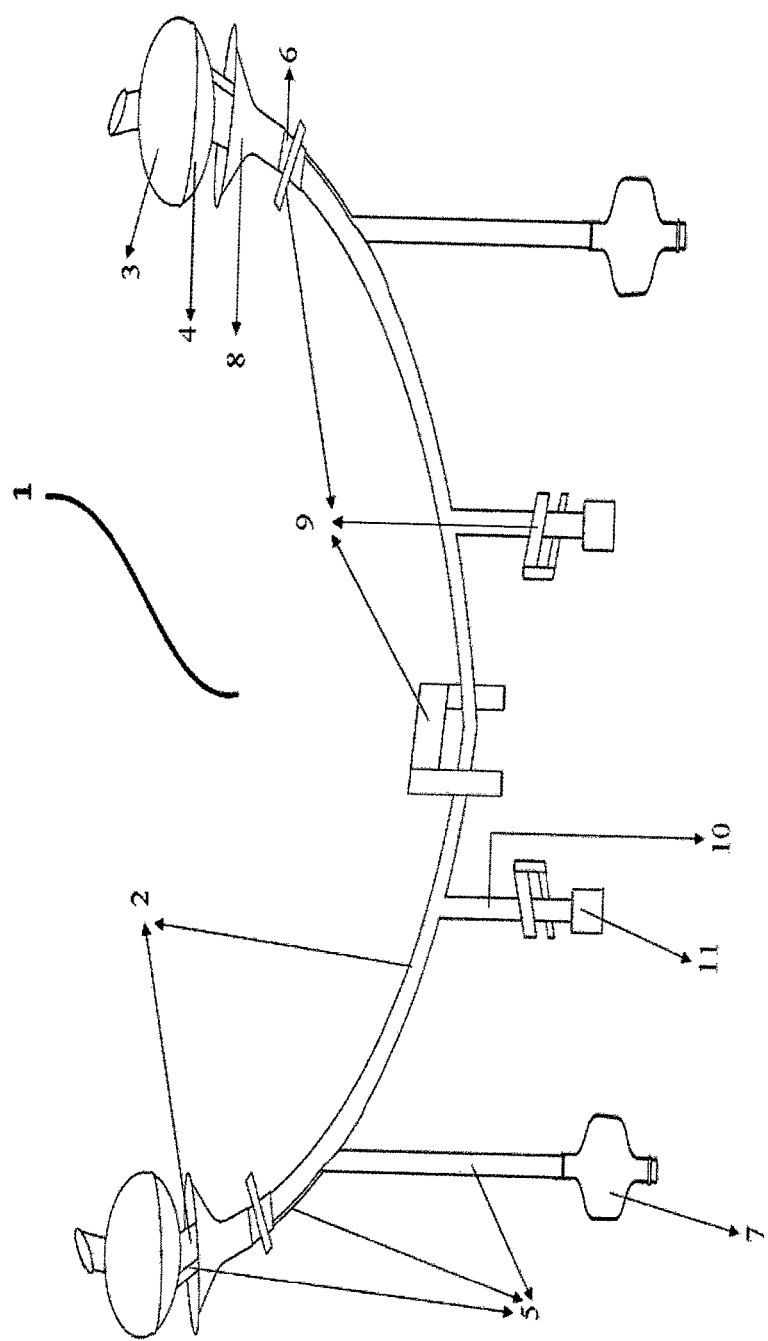

of the balloon (3); protective segment (6) surrounding externally the first path (2) and second path (5), thus preventing their blockage when compressed, that may have various lengths from back end of the balloon (3) to the backside of the catheter (1), that is monolithic along with the first path (2) and the second path (5); cover (8) that prevents the catheter apparatus (1) going out of the vein or its movement, that is located on body side of the catheter apparatus (1), positioned on back of the balloon (3), that can be moved over the catheter apparatus (1) as it is wider than body of the catheter apparatus (1), that has flexible structure having both ends open, that can have the shape of funnel or circle or ellipsis or different shapes; clamping apparatus (9) used to fix the cover on its relevant location; at least one third path (10) in the shape of pipe with both ends open, whose one end is positioned within first path (2), other end is located out of first path (2) and used to draw the liquid or air; connection apparatus (11) that is integrated with outer back end of third path (10) and that enables connection with the external injector and the catheters.

2 Claims, 5 Drawing Sheets

(52) U.S. Cl.
CPC .. *A61M 25/1011* (2013.01); *A61M 25/10186* (2013.11); *A61B 2017/1107* (2013.01); *A61B 2017/1135* (2013.01); *A61M 2025/1061* (2013.01); *A61M 2025/1081* (2013.01)

(58) Field of Classification Search
CPC .. A61M 2025/1061; A61M 2025/1081; A61M 25/1011
See application file for complete search history.

(56) References Cited

U.S. PATENT DOCUMENTS

| | | |
|---|---|---|
| 2001/0001825 A1 | 5/2001 | Snow et al. |
| 2013/0079731 A1 | 3/2013 | Chomas et al. |

OTHER PUBLICATIONS

Written Opinion of the ISA, dated Jul. 24, 2015 for corresponding International Application No. PCT/TR2014/000478.

CATHETER MAINTAINING BLOOD FLOW BY VEIN BYPASS

CROSS-REFERENCE TO RELATED APPLICATIONS

This application is a U.S. National Phase application, under 35 U.S.C. § 371, of International Application no. PCT/TR2014/000478 with an international filing date of Nov. 28, 2014, and which is hereby incorporated by reference for all purposes.

TECHNICAL FIELD

The invention is related to the catheter and vein repair method that enables vein repair surgeries without any bleeding and without hindering blood flow in veins through bypass of the blood flow in the vein to be operated and by preventing any diseases arisen due to stop of blood flow of the organ fed by the associated vein and that sustains blood flow by means of vein bypass in the course of vascular surgeries implemented for surgical processes related to veins in human body.

STATE OF THE ART

Specific tumors, such as lung cancer, grow and reach out major veins. One of the examples is occlusion of the vein due to invasion of superior vena cava (SVC) in the scope of right lung driven tumors. Another example observed in the scope of mediastinal tumors is the vascular occlusion arisen due to invasion of major veins by tumors.

Invasion of major veins by lung tumors inhibits surgical treatment of these cancers. Therefore, these patients are administered with chemoradiotherapy treatment or receive surgical treatment under great risks.

Aneurysm happening on major veins, such as aorta, is difficult to treat, requires surgical treatment in the course of which great complications may occur. For example, life threatening bleedings and damage on organs fed by this vein during surgical operation are some of the risks that may be encountered.

Vascular diseases, such as occlusion or aneurysm through tumor invasion are treated with endoscopic methods and by means of stent placement. However, such proceedings cannot be performed at any health center and by any specialist physician. Many complications can arise in the course of such treatments. Adjoining vascular occlusion and organ damage, thrombus split from blood vessel walls, i.e. embolism causing damage on organs, vein tear and fatal bleedings all serve as an example of aforementioned risks.

Lung and mediastinum tumors can, in some cases, invade to SVC and inferior vena cava (IVC), which may result with progression of obstruction findings in these veins (like SVC syndrome). Cases with tumors having SVC involvement can be treated with extended resections wherein partial or subtotal resection and reconstruction of vein can be applied. However, complication risk of this attempt is high and it can merely be performed at specific centers and by the surgeons having great experience in this scope. In addition, venous blood flow from upper half of the body is blocked by placing clamp on distal and proximal of the region where the mass is invaded to the vein. In other words, blood flow in the vein is stopped.

As a result;
1) Cardiac flow is decreased due to blocking of venous return,
2) Cerebral edema due to prevention of cerebral venous return,
3) Short time period left for main pathology treatment (removal of tumor invading vein and vein repair) as time period allowed for stop of venous blood flow should not be long.

In conclusion, difficult and risky operation process is experienced and the patient may be subject to undesired complications.

On the other hand, aneurism and dissection of large arteries, such as Aorta, are life-threatening diseases. Open surgery and closed (stent placement endoscopically) operations are carried out for treatment of such disorders. However, the cardiopulmonary bypass pump should be used in the scope of open surgery that poses a risk in terms of some patients. Stent placement through closed method can only be performed at selected cases and by experienced teams. Stent placement endoscopically can result with embolus formation in relation with break of plaques on veins and can require shifting to open surgery immediately due to inappropriate placement of stent or injury on vein.

In the state of the art, it may be commented that any method, which easily treats major vascular diseases, has not been developed yet.

One of the methods is the patent application with publication no "WO2013079731 (A1)" and heading "Flow Directional Infusion Device". This invention relates to a device that can be used when any swelling on any region of the vein is in question. If the vein swells completely, this device cannot be used and does not eliminate the problems related with the current technique.

Consequently, a need to develop catheter maintaining blood flow by vein bypass and vein repair method has arisen due to above explained drawbacks and insufficiency of current solutions.

BRIEF DESCRIPTION OF THE INVENTION

Present invention is related to catheter maintaining blood flow by vein bypass and vein repair method, which meets all above mentioned requirements, eliminates all pitfalls and brings specific advantages.

The object of the invention is improvement of single use catheter that sustains blood flow between distal and proximal of vein lesions to be repaired by implanting the catheter maintaining blood flow through vein bypass of the present invention on the vein. In this way, surgical treatment on veins shall be carried out easily, any damage on organ or organs fed by such veins shall be prevented and any risk of bleeding shall be eliminated.

Further aim of the invention is to enable easy surgical treatment of the vein on which the catheter maintaining blood flow by vein bypass of the present invention is implemented.

Another object of the invention is to prevent any damage on organ or organs fed by the vein on which the catheter maintaining blood flow by vein bypass of the present invention is implemented.

Another object of the invention is to eliminate any risk of bleeding on organ or organs fed by the vein on which the catheter maintaining blood flow by vein bypass of the present invention is implemented.

The catheter maintaining blood flow by vein bypass of the present invention ensures more effective and comfortable operation in terms of both the patient and the surgeon by maintaining blood flow within vascular lesion region through an alternative way in the scope of vascular surgery wherein surgical operation is to be implemented due to tumor, aneurism or any other reason.

The structural properties and characteristics and all advantages of the invention can be clearly understood with below drawings and detailed descriptions of the drawings and assessment should be made considering these drawings and their detailed descriptions.

DRAWINGS OF THE INVENTION

"Catheter maintaining blood flow by vein bypass and vein repair method", which is subject of this application, is shown in enclosed drawings, which are listed as following;

FIG. 1: Perspective view showing catheter apparatus maintaining blood flow by vein bypass of the present invention.

Figure 2:
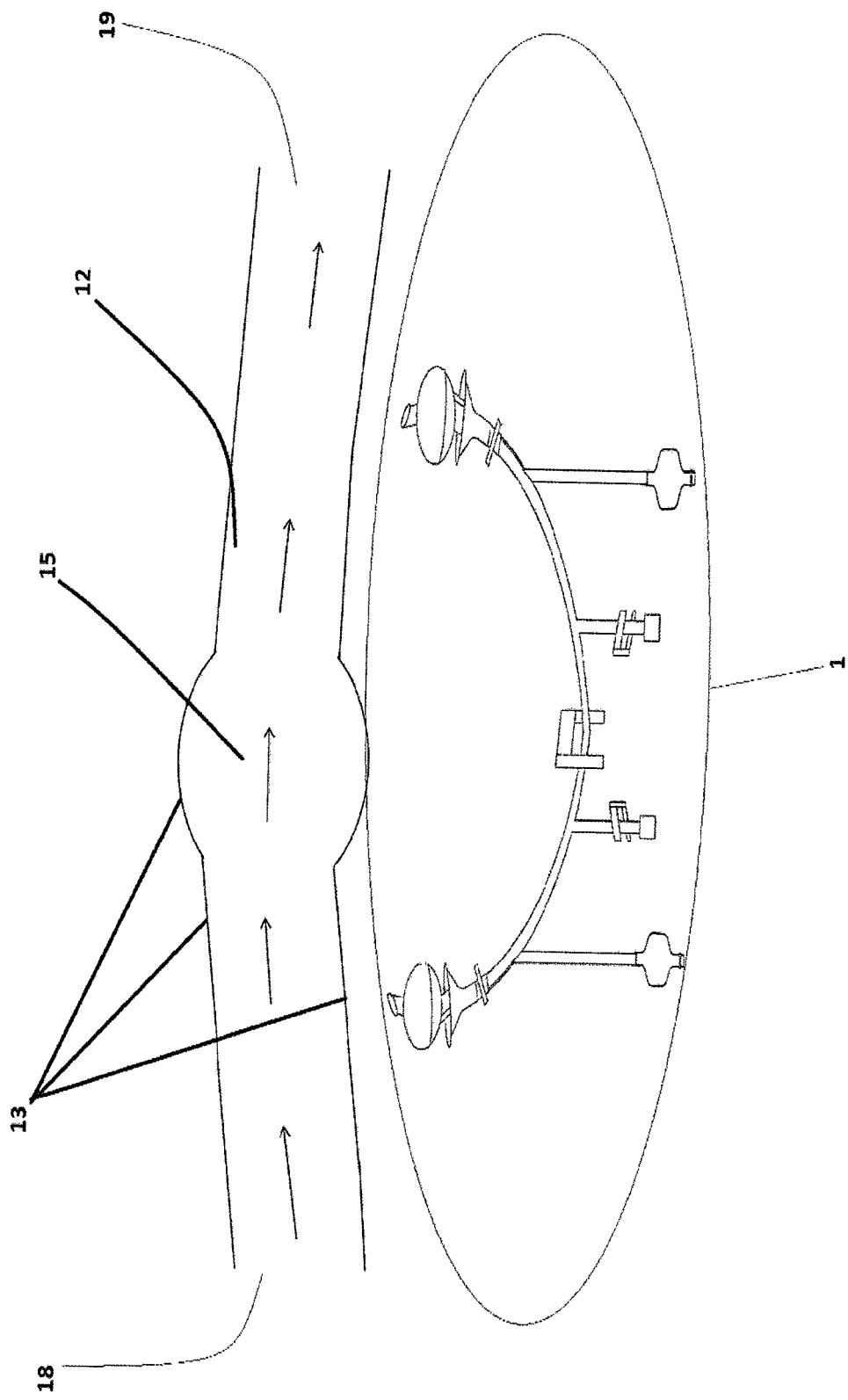
Figure 3:
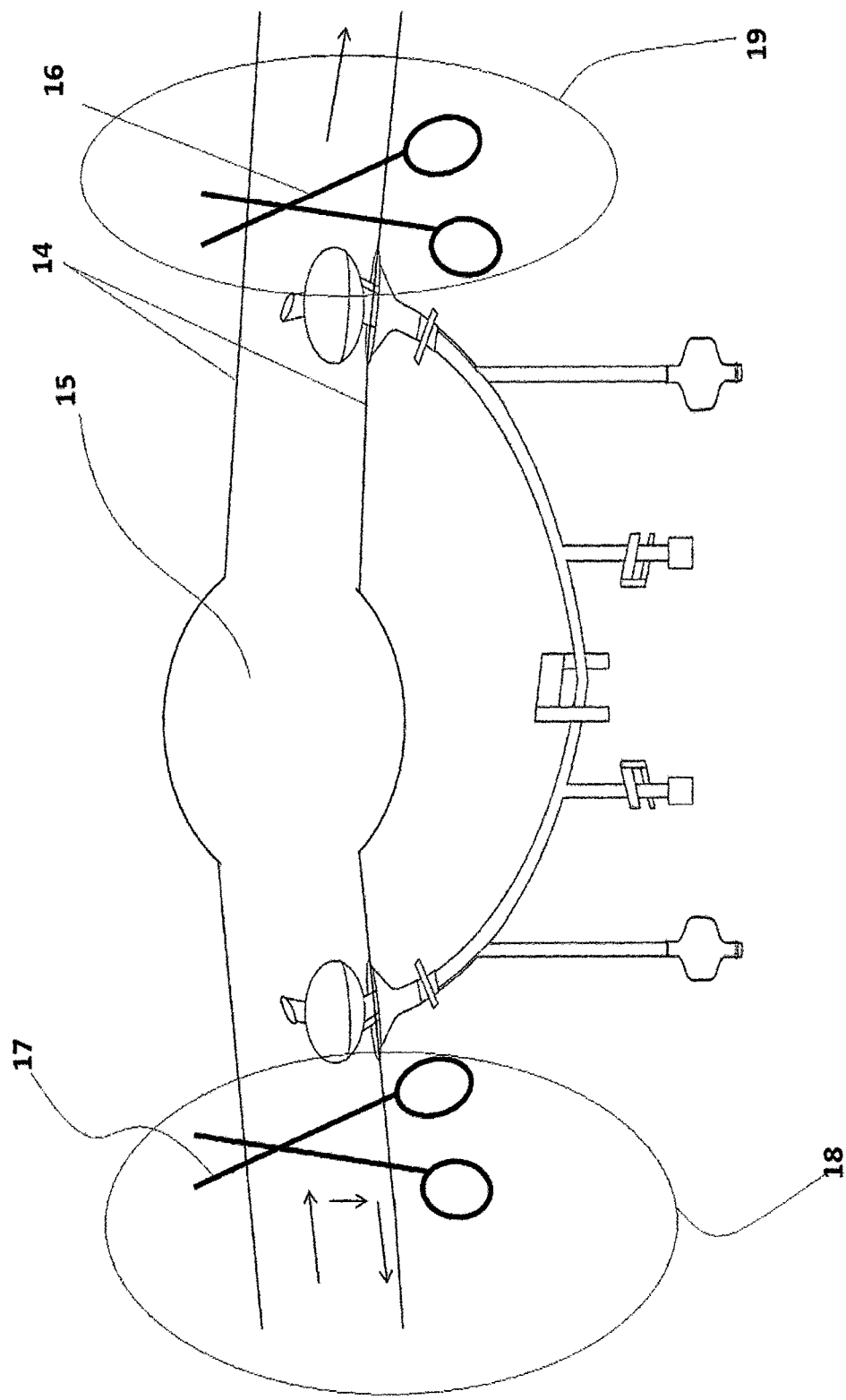
Figure 4:
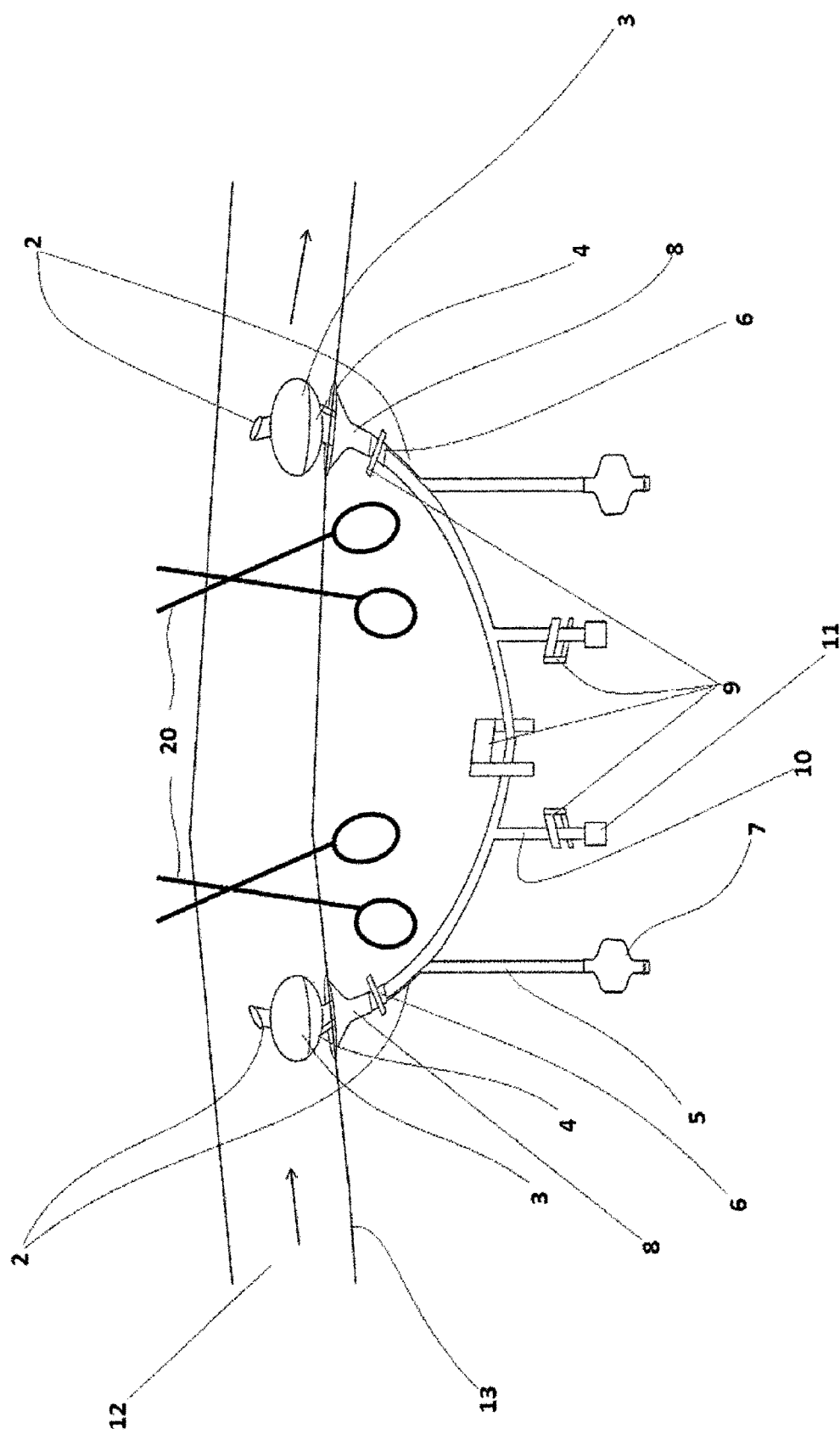
Figure 5:
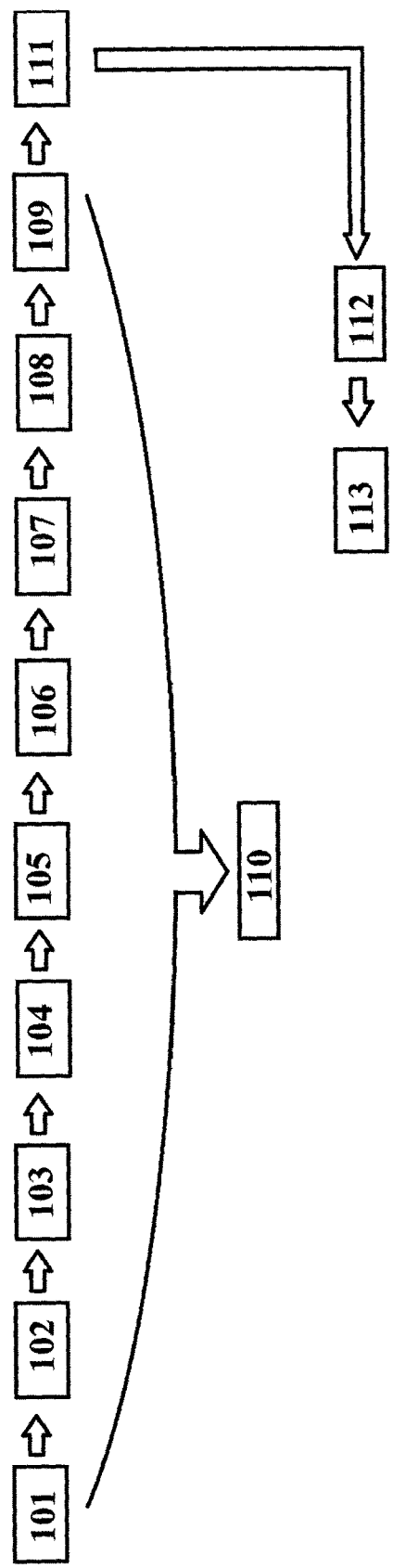

FIG. 2: Drawing that shows the catheter apparatus maintaining blood flow by vein bypass of the present invention and the vein FIG. 3: Drawing that shows the catheter apparatus maintaining blood flow by vein bypass of the present invention and the processing of vein repair method FIG. 4: Drawing that shows the catheter apparatus maintaining blood flow by vein bypass of the present invention and the processing of vein repair method FIG. 5: Drawing that shows the process steps of vein repair method of the catheter apparatus maintaining blood flow by vein bypass of the present invention and the processing of vein repair method Drawings should not be necessarily scaled and unnecessary details for understanding the invention may be omitted. Other elements that are at least mainly equivalent to each other or that have at least mainly equivalent functions to each other are indicated with the same number.

DESCRIPTION OF PART REFERENCES

1. Catheter apparatus
2. First path
3. Balloon (s)
4. Protective layer(s)
5. Second path(s)
6. Protective segment(s)
7. Check valve(s)
8. Cover(s)
9. Clamping apparatus
10. Third path(s)
11. Connection apparatus
12. Vein
13. Vein wall
14. Healthy vein tissue
15. Vein lesion
16. Distal clamp
17. Proximal clamp
18. Proximal side
19. Distal side
20. Clamp

DESCRIPTION OF PROCESS STEPS

101—Placing end of catheter apparatus (1) by making small incision on healthy vein tissue (14) between the proximal clamp (17) and vein lesion (15),
102—Inflation of the balloon (3) within the vein (12) by means of check valve (7) and second path (5),
103—Leaning of the catheter (1) against the vein wall (13) by slightly pulling it out of the vein wall (13),
104—Pushing the cover (8) from outer side of the vein wall (13) towards the vein wall (13) and its pressing with clamping apparatus (9),
105—Placement of other end of catheter apparatus (1) through small incision made on healthy vein tissue (14) between the distal clamp (16) and vein lesion (15),
106—Inflation of the balloon (3) within the vein (12) by means of check valve (7) and second path (5),
107—Leaning of the catheter (1) against the vein wall (13) by slightly pulling it out of the vein wall (13),
108—Pushing the cover (8) from outer side of the vein wall (13) towards the vein wall (13) and its pressing with the clamping apparatus (9),
109—Reflow of the blood inward the vein (12) by slightly opening the proximal clamp (17),
110—If air enters into the vein (12), discharge of the air out of the vein (12) through the third path (10) and without opening the distal clamp (16),
111—Placement of two clamps (20) on regions where vein lesions (15) are observed on both ends of the catheter apparatus (1) and bypassing the vein to the diseased region to enable orientation of the blood flow into the first path (2) and its progression toward other end of the vein (12),
112—After completion of surgical repair, release of catheter apparatus (1), clamping apparatus (9) and the cover (8) on proximal side (18),
113—Deflation of the balloon (3) by means of the check valve (7) and the second path (5) and pulling the catheter apparatus (1) back.

DETAILED DESCRIPTION OF THE INVENTION

In this detailed description, the preferred embodiments of catheter maintaining blood flow by vein bypass and vein repair method of the present invention are only described for better understanding the invention without causing any limiting affect.

Furthermore, some components in the detailed description can be used in various forms for better understanding and content integrity in the sentence. Components in various statements represent the component with the same number.

Catheter apparatus (1) is the catheter of the present invention that sustains the blood flow by vein bypass, is made of any plastic and similar raw materials, open on both ends and comprises of first path (2), balloon (3), protective layer (4), second path (5), check valve apparatus (7), protective segment (6), cover (8), clamping apparatus (9), third path (10), connection apparatus (11).

First path (2) comprises one balloon (3) on the point close to its both ends and protective layer (4) is available on its topside.

Balloon(s) (3) is the component stopping blood flow within the vein when it is placed within the vein thanks to its inflation deflation feature and over which protective layer (4) is available.

Protective layer(s) (4) is the component positioned on the balloon (3) and strengthening the balloon.

Second path(s) (5) is the discharge flow path connected to the first path (2) that enables inflation and deflation of the balloon (3).

Protective segment(s) (6) is the component positioned on first path (2) and preventing damage of the clamping apparatus (9) on the first path (2).

Check valve(s) (7) is the component that provides intake of air required for inflation of the balloon (3) and that discharges the air within the vein over the catheter apparatus (1).

Cover(s) (8) is the component that prevents the catheter apparatus (1) going out of the vein (12) or its movement, that is located on body side of the catheter apparatus (1), positioned on back of the balloon (3), that can be moved over the catheter apparatus (1) as it is wider than body of the catheter apparatus (1), that has flexible structure having both ends open, that can have the shape of funnel or circle or ellipsis or different shapes.

Clamping apparatus (9) is the component used to keep the cover (8) in fixed position.

Third path(s) (10) is the component with both ends open, whose one end is positioned within first path (2), other end is located out of first path (2) and used to discharge the air emerging in the vein (12) and if necessary, that enables flow of the blood out of the vein (12) and the catheter apparatus (1).

Connection apparatus (11) is the component that is integrated with outer back end of third path (10) and that, if necessary, enables connection with the external injector and the catheters.

The vein (12) is the blood flow path where blood circulation in human body is maintained.

Vein Wall (13) is the vein (12) external surface that surrounds and forms the vein (12) and in which the blood flows.

Healthy vein tissue is the healthy vein (14) part that is available in the beginning and at the end of the region where vein lesion (15) exists.

Vein lesion (15) is the part of vein (12) where tumor, edema and similar diseases occurred within the vein (12).

Distal clamp (16) refers to the clamp (20) positioned on distal side (19) on the vein (12).

Proximal clamp (17) refers to the clamp (20) positioned on proximal side (18) on the vein (12).

Proximal side (18) is the part before Vein lesion (15) on the vein (12) where the blood is flowing.

Distal side (19) is the part of blood flow after its passage through the Vein lesion (15) on the vein (12).

Clamp (20) is the clamping apparatus that ceases blood flow during surgical interventions.

Application of Catheter Maintaining Blood Flow by Vein Bypass and Vein Repair Method of the Present Invention:

Through a small incision on healthy vein tissue (14) between the proximal clamp (17) and the vein lesion (15), end of the catheter apparatus (1) is placed. The balloon (3) is inflated in the vein (12) by means of check valve (7) and second path (5). By slightly pulling the catheter (1) out of the vein wall (13), the catheter (1) leans on the vein wall (13). The cover (8) is pushed towards the vein wall (13) from external side of the vein wall (13) and pressed with clamping apparatus (9), in this way, movement of the catheter apparatus (1) out of the vein (12) or inside of the vein (12) is prevented and it is fixed.

Other end of the catheter apparatus (1) is inserted through the small incision on healthy vein tissue (14) between the distal clamp (16) and the vein lesion (15). The balloon (3) is inflated in the vein (12) by means of check valve (7) and second path (5). By slightly pulling the catheter (1) out of the vein wall (13), the catheter (1) leans on the vein wall (13). The cover (8) is pushed towards the vein wall (13) from external side of the vein wall (13) and pressed with clamping apparatus (9), in this way, movement of the catheter apparatus (1) out of the vein (12) or inside of the vein (12) is prevented and it is fixed.

Proximal clamp (17) is gently opened and reflow of blood into the vein (12) is provided. Meanwhile, air leakage into the vein (12) may be possible during execution of above explained process steps. This air should be taken out of the vein (12). In this scope, third path (10) is used. By opening third path (10) before the distal clamp (16), air is discharged from the third path (10). Distal clamp (16) is opened after it is ensured that any air is not available in the vein (12). In this stage, blood flows through both vein (12) and the catheter apparatus (1). In other words, two flows occur over the vein (12).

Two clamps (20) are placed on both ends of the catheter apparatus (1) on the sides where vein lesion (15) exists. Thus, the blood flow is directed towards the first path (2) where the blood flows and progresses to the other end of the vein (12). In other words, diseased region of the vein (12) is bypassed where the blood flow is prevented. As there is not any blood flow in this region, there exists no risk of remaining bloodless of the organs. Any vein (12) repair process is performed safely and leisurely without any risk of vein (12) bleeding.

After completion of surgical repair, clamping apparatus (9) and the cover (8) of the catheter apparatus (1) in proximal side (18) is loosened and the balloon (3) is deflated through the check valve (7) and the second path (5). End of the catheter apparatus (1) is pulled back.

Clamping apparatus (9) and the cover (8) of the catheter apparatus (1) in distal side (18) is loosened and the balloon (3) is deflated through the check valve (7) and the second path (5). End of the catheter apparatus (1) is pulled back.

The invention claimed is:

1. A catheter apparatus (1) maintaining blood flow by vein bypass, made of a plastic and similar raw materials, that is open on both ends, characterized in that the catheter apparatus comprises:
   a first path connecting both ends,
   one balloon (3) on a point close to each of both ends,
   a protective layer (4) positioned on each of the balloons (3),
   a second path (5) enabling deflation and inflation of the balloons (3), having a monolithic pipe shape adhered side by side to the first path (2), whose one open end terminates within the balloon (3),
   a check valve apparatus (7) that is monolithic with a back end of the second path (5) and provides substances such as air and liquid with an external injector for inflation and deflation of the balloon (3),
   a protective segment (6) surrounding externally the first path (2) and second path (5), thus preventing blockage of the first path and second path when compressed, the protective segment configured to have various lengths from a back end of the balloon (3) to a backside of the catheter (1), and is monolithic along with the first path (2) and the second path (5),
   a cover (8) that prevents the catheter apparatus (1) from going out of the vein or movement of the catheter apparatus, that is located on a body side of the catheter apparatus (1), positioned on the back of the balloon (3), that can be moved over the catheter apparatus (1) as it is wider than a width of the body of the catheter apparatus (1), that has a flexible structure having both ends open, configured to have a shape of a funnel or a circle or an ellipsis or different shapes, a clamping apparatus (9) used to fix the cover on a relevant location, at least a third path (10) in the shape of a pipe with both ends open, having one end positioned within the first path (2), another end located out of the first path (2) and used to draw the liquid or air, a connection apparatus (11) that is integrated with an outer back end of the third path (10) and that enables connection with the external injector and catheters.

2. The catheter apparatus (1) according to claim 1, characterized in that the cover (8) and clamping apparatus (9) are integrated to each other or have a monolithic structure.

* * * * *